United States Patent [19]
Lentini

[11] Patent Number: 5,885,557
[45] Date of Patent: Mar. 23, 1999

[54] COMPOSITIONS USEFUL IN THE PHOTOTHERAPEUTIC TREATMENT OF PROLIFERATIVE SKIN DISORDERS

[75] Inventor: Peter J. Lentini, Bayside, N.Y.

[73] Assignee: Estee Lauder Inc., New York, N.Y.

[21] Appl. No.: 598,297

[22] Filed: Feb. 8, 1996

[51] Int. Cl.$^6$ ..................................................... A61K 7/42
[52] U.S. Cl. .............................. 424/59; 514/675; 514/863
[58] Field of Search ........................ 424/59, 60; 514/863, 514/675

[56] References Cited

U.S. PATENT DOCUMENTS

| | | | |
|---|---|---|---|
| 2,949,403 | 8/1960 | Andreadis et al. | 167/90 |
| 4,325,965 | 4/1982 | Chiba | 424/284 |
| 4,454,159 | 6/1984 | Musher | 424/358 |
| 4,651,739 | 3/1987 | Oseroff et al. | 128/395 |
| 4,708,865 | 11/1987 | Turner | 424/59 |
| 4,981,681 | 1/1991 | Tosti | 424/78 |
| 5,112,613 | 5/1992 | Honda et al. | 424/400 |
| 5,122,536 | 6/1992 | Perricone | 514/474 |
| 5,126,135 | 6/1992 | Yamada et al. | 424/679 |
| 5,556,612 | 9/1996 | Anderson et al. | 424/59 |

FOREIGN PATENT DOCUMENTS

56773/60  9/1962  Australia .

OTHER PUBLICATIONS

Hruza, "Maximally Aggressive Phototherapy of Psoriasis Using Selectively Desquamating Topical Photoprotectants", 4th annual Photomedicine Conference, St. Louis, Missouri, Feb. 3, 1995.
Levy, "dihydroxyacetone–Containing Sunless or Self–Tanning Lotions", J. Am. Acad. Dermatol. 27:989–93 (1992).
Lui et al., "Photodynamic Therapy in Dermatology", arch Dermatol. 128:1631–1636 (1992).
McCullough et al., "Low Dose Photofrin Photodynamic Therapy of Psoriasis", Clin. Res. 39:509A (1991).
Carabott and Hawk, "A Modified Dosage Schedule For Increased Efficiency In PUVA Treatment of Psoriasis", Clin. and Exp. Derm. 14:337–340, (1989).
Follett et al., "Protection of Photosensitized Rats Against Long Ultraviolet Radiation by Topical Application of Compunds With Structures Similar to That of Dihydroxyacetone", Dermatologica, 175:58–63 (1987).
Hönigsmann et al., "Oral Photochemotherapy With Psoralens and UVA (PUVA): Principles and Practice", Dermatology In General Medicine 3rd Ed., McGraw Hill, New York (1987).

Takahashi et al., "Measurement of Turnover Time of Stratum Corneum Using Dansyl Chloride Fluorescence", J. Soc. Cosmet. Chem., 38:321–331 (1987).
Weinstein et al., "Cell Kinetic Basis for Pathophysiology of Psoriasis", J. Invest. Dermatol. 85(6):579–583 (1985).
Ryatt et al., "The Usefulnes of Reflectance Spectorphotometric Measurements During Psoralens and Ultrviolet A Therapy for Psoriasis", J. Am. Acad. Dermatol. 9:558–562 (1983).
Parrish et al., "Photochemotherapy of Skin Diseases", The Science of Photomedicine, Plenum Press, New York (1982).
Parrish and Jaenicke, "Action Spectrum For Phototherapy of Psoriasis", J. Invest. Dermatol., 76(5):359–362 (1981).
Wolff and Hönigsmann, "Clinical Aspects of Photochemotherapy", Pharma. Ther. 12:381–418 (1981).
"Research Needs in 11 Major Areas In Dermatology", J. Invest. Derm., 73:402–413 (1979).
Stern et al., "Risk of Cutaneous Carcinoma in Patients Treated With Oral Methoxsalen Photochemotherapy for Psoriasis", J. Med. 300(15):809–813 (1979).
Maibach and Kligman, "Dihydroxyacetone: A Suntan–Simulating Agent", Arch. Dermatol., 74:505–507 (1960).
Fowlks, "The Chemistry of the Psoralens", J. Invest. Derm. vol. 32, pp. 249–254 (1959).
Fitzpatrick and Pathak, "Historical Aspects of Methoxsalen and Other Furocoumarins", J. Inves. Derm., pp. 229–231 (1958).
Fowlks, "The Mechanism of the Photodynamic Effect", J. Inves. Derm., pp. 233–247 (1958).
Pathak, and Fizpatrick, "Relationship of Molecular Configuration to the activity of Furocoumarins Which Increase the Cutaneous Responses Following Long Wave Ultraviolet Radiation", J. Inves. Dermatol., pp. 255–262 (1958).

Primary Examiner—Jose G. Dees
Assistant Examiner—Michael A. Williamson
Attorney, Agent, or Firm—Pennie & Edmonds LLP

[57] ABSTRACT

This invention relates to compositions useful in the phototherapeutic treatment of psoriasis and other proliferative skin diseases. The compositions of the present invention comprise dihydroxyacetone and a penetration attenuator, both in a cosmetically and/or pharmaceutically acceptable carrier. Optionally, the compositions of the present invention may also contain an acidic component. The compositions of the present invention are useful in the exploitation during phototherapeutic treatment of the hyper-desquamation characteristics of the psoriatic or otherwise affected skin.

15 Claims, No Drawings

COMPOSITIONS USEFUL IN THE PHOTOTHERAPEUTIC TREATMENT OF PROLIFERATIVE SKIN DISORDERS

1. FIELD OF THE INVENTION

This invention relates to compositions useful in the treatment of psoriasis and other proliferative skin diseases. More specifically, the invention relates to compositions useful for treating psoriasis and other proliferative skin diseases by phototherapeutic techniques, wherein the compositions comprise dihydroxyacetone.

2. BACKGROUND OF THE INVENTION

2.1. Compositions Containing Dihydroxyacetone

Dihydroxyacetone ("DHA") is a white, crystalline, hygroscopic powder having the chemical formula $C_3H_6O_3$. DHA is a three-carbon sugar, normally found as a dimer in freshly prepared aqueous solutions. U.S. Pat. No. 2,949,403 discloses compositions and methods of using DHA as a tanning agent for the human epidermis. When applied topically, DHA penetrates superficially into the stratum corneum where it covalently binds to epidermal proteins via their amino groups, producing a cosmetically-acceptable "tan" color.

U.S. Pat. No. 2,949,403 discloses that DHA may be used in concentrations varying from 0.05 to about 90.0 percent by weight. However, commercial tanning products typically contain only up to about 5% DHA because higher concentrations do not provide an acceptable artificial tan. Occasionally, self-tanning compositions may contain as much as 7.5% DHA. The amount of DHA present in these products depends on a number of factors, including the difficulty in formulating acceptable compositions with higher concentrations of DHA. Likewise, a concentration of about 5% DHA is usually sufficient to provide the coveted artificial "tan" coloring. Many times, higher concentrations of DHA result in skin color much darker or different in color than the desired "tan" color sought to be duplicated.

Particularly, higher concentrations provide color that do not resemble natural tans or darkens the skin to an unacceptable level for the consumer.

Since the 1960's, several compositions using DHA as an active ingredient to impart an artificial tan have been disclosed. For example, U.S. Pat. No. 4,708,865 discloses a topical solution containing DHA and various dyes to offset the undesirable orange cast or hue which results from the use of DHA on fair skinned individuals.

Further, it is well known to formulate DHA into a variety of different carriers such as oil-in-water emulsions, preparations containing up to 50% alcohol, creamy bases and other conventional carrier systems such as lotions, ointments, dusting powders and the like. These compositions typically include a number of other optional ingredients such as perfumes, preservatives, emollients, antiseptics, pigments, dyes, humectants, as well as other materials that may be cosmetically or medicinally desirable. In particular, many commercial products contain materials which act as penetration enhancers in that they promote the absorption of the DHA deep into the skin tissue layers in order to increase the length of time the artificial tan remains.

In addition to its ability to elicit an artificial tan on human skin, it is also known that the reaction product of DHA and compounds in the skin tissue which produces the "tan" color is an effective sunscreening agent. In particular, this reaction product is known to absorb ultraviolet light in the 300–600 nanometer range, with a peak at about 350 nanometers, thus protecting the skin from damage due to exposure to such radiation.

2.2. Phototherapeutic Treatment of Proliferative Skin Diseases

Proliferative skin diseases, such as psoriasis, eczema, mycosis fungoides, actinic keratosis, and lichen planus, are known to effect one to two percent of the U.S. population, with as many as 150,000–260,000 new cases occurring annually ("Research Needs in 11 Major Areas in Dermatology" I. Psoriasis. *J. Invest. Dermatol.* 73:402–13, 1979). One method used to treat the rapid proliferation of skin cells is phototherapy, which utilizes optical absorption of ultraviolet (UV) radiation by the skin to kill rapidly growing cells and arrest proliferation. At present, both UVA and UVB therapy, which expose the skin to UV radiation between 320–400 nm (UVA radiation) or 290–320 nm (UVB radiation), are effective and widely used. PUVA therapy, a form of photochemotherapy which involves repeated topical application of psoralen or a psoralen-based compound to an affected region of skin, followed by exposure of that region to UVA radiation, is also widely used. Another method used to treat proliferative skin diseases, particularly psoriasis and mycosis fungoides, is photodynamic therapy (PDT). In this method, a photosensitizing agent, which is a drug selectively retained in carcinoma cells, is administered to a patient. Following absorption of light (typically between 320–700 nm, depending on the drug) the photosensitizing agent undergoes a photochemical reaction, resulting in the production of cytotoxic singlet oxygen which eventually leads to tumor vessel destruction in the skin (Anderson, et al., *Arch. Dermatol.* 128:1631–1636, 1992).

Prolonged treatment for proliferative skin diseases using these types of therapies can, however, result in significant acute and chronic adverse effects including erythema, pruritus, skin cancer, and chronic light-induced damage of the skin (Stern et al., *N.E.J. Med.* 300:809–812, 1979).

It is therefore desirable to reduce the number of times the skin is exposed to radiation during phototherapy. PUVA therapy (Wolff, *Pharmacol. Ther.* 12:381, 1981), and frequent alternation of PUVA therapy with other treatments (Parris et al., *The Science of Photomedicine*, Regan et al., eds., 1982, p. 615) have been suggested as methods to reduce the cumulative number of iterations (typically around 25) required for successful treatment. Another method used to decrease the number of phototherapy treatments involves increasing the optical fluence during therapy (Honigsmann et al., *Dermatology in General Medicines,* 3rd ed, T. B. Fitzpatrick et al., eds., 1533–1558, 1987; Ryatt, et al., *J. Am. Acad. Dermatol.* 9:558–562, 1983). Up to a threefold reduction in the time required for the affected region to clear is possible when isolated plaques are exposed to radiation levels between two and three times the minimal erythema dose (NED), defined as the level of optical fluence resulting in the onset of erythema (Parrish et al., *J. Invest. Dermatol.* 76:359–362, 1981).

Because both UVA and UVB radiation are harmful to normal skin, the tolerable limit of treatment aggressiveness is ultimately limited by adverse effects resulting from the cumulative exposure of the skin to UV radiation. Presently, the level of UV radiation is kept as high as possible during phototherapeutic treatments, just less than the level causing painful sunburn.

In order to reduce the effects of increased exposure to UV radiation during phototherapy, it is possible, but impractical, to apply sunscreens to all the non-affected skin areas which surround sites of affected skin; most proliferative skin diseases involve tens or hundreds of affected regions which are randomly located over the body. In addition, during PDT there is often appreciable uptake of the photosensitizing agent in the non-affected regions of skin, making it desirable to protect these regions from drug-activating radiation.

DHA has been used in phototherapeutic treatment of proliferative skin disorder previously. (See, "Dihydroxyacetone (DHA) Enhanced Photochemistry of Psoriasis" L. Hruza et al. 4th annual Photo-medicine Conference, New Orleans (Feb. 3, 1995). Nonetheless, there has been and continues to be a need for DHA formulations specifically suited for PUVA treatment and which have improved activity.

3. SUMMARY OF THE INVENTION

The compositions of the present invention comprise DHA and a penetration attenuator, both in a cosmetically and/or pharmaceutically acceptable carrier. Certain of the compositions are uniquely formulated for use in PUVA phototherapy. The DHA binds to portions of the stratum corneum to partially absorb optical radiation e.g., ultraviolet radiation. The penetration attenuator prevents the DHA from penetrating beyond the uppermost tissue layers, thereby promoting a more rapid "sloughing off" of the DHA-induced tan from the affected areas of the skin. Optionally, the compositions of the present invention may also contain an acidic component, which serves to stabilize the formulation and optimize its pH, as well as promote faster reaction of the DHA with the healthy, unaffected skin tissue.

In preferred embodiments, the compositions of the present invention are used to treat psoriasis, mycosis fungoides, eczema, actinic keratosis, or lichen planus. Other features and advantages of the invention will be apparent from the following description of the preferred embodiments thereof, and from the claims.

The present invention relates to compositions useful in phototherapeutic treatments of proliferative skin disorders in a human patient having affected and non-affected areas of skin. The term "proliferative skin disorder", as used herein, refers to psoriasis, eczema, actinic keratosis, mycosis fungoides, lichen planus, and other diseases resulting in rapid proliferation of skin cells.

The phototherapeutic treatment of proliferative skin disorders employing the compositions of the present invention typically features the steps of: (a) topically applying a sunscreen providing photo-protection to the affected and non-affected areas of skin; (b) waiting for a time period sufficient for the skin of the affected areas to be sloughed off to a greater degree than skin of non-affected areas; and, (c) exposing the affected and non-affected areas of skin of the patient to a selected level of optical radiation sufficient to treat the affected areas of skin and insufficient to cause significant damage to the non-affected areas of skin.

One essential feature of proliferative skin disorders that is used to advantage in the phototherapeutic method of the treatment is that of hyper-proliferation of the epidermis, the outer layer of skin. Affected regions of skin grow and are sloughed off at a rate of about ten times than that of non-affected regions. A topically-applied substance, such as a sunscreen, adhering to the stratum corneum of the affected regions will therefore be sloughed off much faster relative to sunscreen applied to the non-affected regions. After a predetermined period of time, this results in the non-affected regions of skin retaining a large amount of sunscreen relative to the affected regions.

Preferably, between steps (b) and (c), the amount of photo-protection provided by the sunscreen to the affected and/or non-affected areas of the patient's skin is determined, e.g., using a non-invasive optical method involving measuring the reflectance properties of sunscreen-treated skin. In alternate embodiments, a photosensitizing agent, psoralen, or a psoralen-based compound is administered to the patient prior to step (c).

4. DETAILED DESCRIPTION OF INVENTION

The compositions of the present invention are useful during phototherapeutic treatments because DHA exhibits desirable chemical and optical properties. The desirable "chemical" properties of DHA include its low toxicity and ability to adhere to both affected and non-affected regions of the skin. Furthermore, DHA is highly substantive, meaning that it is not easily washed off, and adheres to the elements of the stratum corneum (e.g., keratin, other proteins, lipids, etc.) through covalent bonding.

The desirable "optical" properties include the DHA reaction product's relatively broad absorption spectrum in the UV and/or visible frequency range, and its the ability to absorb at least about 50% of the incident radiation. The DHA reaction product does not undergo photodegradation following the absorption of light and minimizes hyperpigmentation of the skin during the phototherapy.

Moreover, DHA possesses a beneficial characteristic in that it colors the skin to which it has been applied. This is of particular advantage in phototherapeutic treatment because it permits the individual providing the treatment to easily determine where the sunscreen compositions have been applied, thus reducing the potential for damaging healthy skin by unintentionally exposing to harmful radiation areas of the skin that have not been properly protected.

The compositions of the present invention are uniquely formulated to exploit the properties of the DHA, to assist or enhance its performance in PUVA therapy and to make the composition acceptable to the skin affliction of the patient. In particular, patients receiving phototherapeutic treatments typically suffer from severely damaged skin, wherein raw skin is exposed. Accordingly, the present compositions are formulated so as to provide as little discomfort upon topical application as possible.

The compositions of the present invention comprise DHA and a penetration attenuator, both in a cosmetically and/or pharmaceutically acceptable carrier. The concentration of DHA in the sunscreen compositions of the present invention is defined as that which is necessary to provide substantial photoprotection to normal mammalian skin. Preferably, the compositions of the present invention contain about 5 to about 20 percent by weight DHA. More preferably, the present compositions contain about 10 to 20 percent by weight DHA. Most preferably, these compositions contain about 15 percent by weight DHA.

The penetration attenuator serves to prevent the DHA from penetrating beyond the uppermost tissue layers of the skin. By preventing the penetration of the DHA, the "tan" and the associated photoprotection imparted to the skin is kept as a strictly surface phenomenon, thereby allowing the "tan" to shed rather quickly from the affected areas of the skin (ebg the psoriatic plaques). If the DHA were allowed to penetrate deeply into the affected areas, it could take a matter of weeks to shed, thereby obviating any benefit of the inherent selectively desquamating properties exploited by the phototherapeutic treatment. Further, the penetration attenuator promotes a more conventional distribution of the sunscreen composition on the healthy, unaffected skin tissue.

Preferably, the penetration attenuator comprises of film-forming materials which have a tendency to either associate with, or provide solubility for, an ingredient, in this case DHA. These film-forming agents are generally large polymers with molecular weights too high to penetrate deeply into skin. By virtue of association, either through weak electrostatic forces, Van Der Walls forces, or through hydrogen bonding, a given material such as DHA can associate more strongly with a polymer than with skin components and because of the size of the polymer, the ingredient associating with the polymer will become immobilized and unable to migrate into skin tissue. By virtue of providing preferential solubility, an ingredient may be more soluble in a given polymer than in skin tissue components. Therefore, if the material shows better solubility in the polymer system than in skin tissue components, and if the polymer is too large to penetrate, then the ingredient in question will not penetrate either.

Any number of polymeric materials are contemplated as being useful as the penetration attenuator of the present invention based upon the criteria discussed in the previous paragraph. General categories of materials exhibiting these associative properties and exhibiting this attenuation include but not limited to, linear and branched polyurethanes, polyethylenes, polyacrylates, polyquaternary cellulosics, and various block and comb copolymers of silicone, pyrrolidone, acrylic acid, methylacrylic acid, etc. In the preferred embodiment of the invention, the penetration attenuator comprises a polyurethane polyol prepolymer commercially available from Barnet, Inc.

The penetration attenuator may be present in an amount sufficient to prevent or inhibit the DHA from penetrating beyond the uppermost layers of the skin, e.g., the stratum corneum. In particular, the penetration attenuator is present in an amount of about 0.2 to about 20.0 percent by weight. Preferably, the compositions of the invention contain about 5.0 to about 15.0 percent by weight penetration attenuator. Most preferably, the compositions contain about 10 percent by weight penetration attenuator.

The DHA and penetration attenuator are applied to the skin via a vehicle or carrier. Any cosmetically and/or pharmaceutically acceptable conventional carrier or vehicle may be employed. Appropriate carriers include lotions, creams, oils, emulsions, gels, tinctures, and ointments. These carriers may be sprayable although spreadable is preferable. One of ordinary skill in the art would readily be able to formulate an appropriate carrier for use in the present compositions.

Optionally, the compositions of the present invention may also contain an acidic component which acts to stabilize the formulation and optimize its pH. Additionally, the acidic component is believed to promote a faster reaction with the unaffected, healthy skin tissue, as well as retard the ability of the staining of the affected tissue by the DHA.

When selecting a particular acid component, it is important to recognize that the present compositions are typically applied directly to the affected areas of the skin. Many times, the affected areas have been severely damaged and raw skin is exposed. Thus, when selecting an acidic component, consideration must be given to minimizing the discomfort associated with the application of the present compositions.

A number of organic and inorganic acids are contemplated for use in the acidic component of the present invention. The skilled artisan would easily be able to determine which organic and/or inorganic acids that are suitable for use in the acidic component. For example, dilute hydrochloric acid is suitable in the acidic component of the compositions. Alpha hydroxy acids are preferred for use in the acidic component. Most preferably, lactic acid is employed in the acidic component of the invention.

The amount of acidic component in the present compositions will varying depending on factors such as the type of acid employed, as well as the concentration and relative strength of the acid. Generally, about 0.1 to about 20.0 percent by weight of acidic component in present in the compositions of the invention. Preferably, about 1.0 to about 5.0 percent by weight of acidic component is employed in the present compositions. Most preferably, about 2 to about 3 percent by weight of acidic component is employed in the present compositions.

Various other optional ingredients may be included in the compositions of the present invention, these include but are not limited to preservatives, emollients, antiseptics, pigments, dyes, humectants, propellants, as well as other classes of materials whose presence may be cosmetically, or medicinally desirable. Common examples can be found in the *CTFA International Cosmetic Ingredient Dictionary* 4th Edition, The Cosmetic, Toiletry, and Fragrance Association, Inc., Washington, D.C., 1991, as well as in *Remington's Pharmaceutical Sciences,* 18th Edition, A. R. Greenaro Ed., Mack Publishing Co., Easton, Pa., 1990. Common examples of such ingredients are provided below by way of example and not limitation.

Optional ingredients include emulsifiers such as Peg-100 Stearate, Glyceryl monostearate, DEA Cetyl Phosphate, dimethicone copolyol, TEA Stearate or suitable ingredients which provide emoliency or humectancy, such as glycerine or Propylene glycol, mineral oil, petrolatum, fatty acid esters, such as myrystal lactate, caprylic and capric triglycerides, dimethicone and natural whole oils or components thereof, moisturizing ingredients, such as wheat lipid extracts or ceramides, preservatives, such as methyl paraben phenoxyethanol, etc.

The application of adherent sunscreens containing active compounds is followed by a period during which preferential loss of skin in the affected regions (i.e., the lesions) occurs because of rapid skin proliferation, leaving these regions with a lower concentration of the sunscreen relative to the non-affected regions. The affected regions of skin are thus left relatively unprotected from optical radiation during phototherapy or PDT. Selectively protecting the non-affected skin with the compositions of the present invention allows: (1) more aggressive phototherapies, leading to an acceleration of the skin clearing process (Carabott et al., *Clin. Exp. Dermatol.* 14:337–340, 1989); (2) reduction in the occurrence of sunburn, skin cancers, and other acute side effects; and, (3) a decrease in the number of treatments necessary for treating rapidly proliferating skin diseases, thus simplifying the therapy. The compositions of the present invention therefore makes treatment of affected skin using phototherapy, PDT or photochemotherapy both safer and more efficient.

4.1. Interaction of DRA vith the Stratum Corneum

Following topical application, the sunscreens compositions bind to proteins contained in the top cell layers of the stratum corneum. Alternatively, they may polymerize or bind with other components of the skin, such as lipids. In the case of DHA, this results in the formation of an oxidized compound which exhibits fluorescent behavior following the absorption of light (Ellis *Adv. Carbohydrate Chem.* 14:63–135, 1959).

In order to determine the depth of staining, samples of psoriatic skin are treated with a single application of DHA solution and then biopsied. Frozen sections of skin are prepared, and the fluorescence of DHA as a function of depth in the skin is measured using standard spectroscopy techniques after 1- and 3-day periods. The fluorescence induced in the DRA stained skin after a 1-day period should be limited to the upper half of the stratum corneum. The intensity of the fluorescence should be significantly reduced after a 3-day period due to sloughing off of the stratum corneum. The fluorescence intensities of the stained skin samples are compared with an unstained control sample in the study.

The depth of DRA penetration can be measured by topically applying a solution of DHA, waiting a period of time sufficient for DHA to penetrate the stratum corneum, and peeling off layers of skin with an adhesive tape while measuring the intensity of the induced fluorescence.

Using a topically-applied sunscreen, a thin layer of DHA is deposited on a section of the forearm of volunteers with normal skin. After allowing sufficient time for the DHA to diffuse into the stratum corneum (4–6 hours) an adhesive tape is applied to the skin in the region of the applied sunscreen. Peeling of the tape results in the removal of approximately one layer of skin cells having a thickness of about 0.5 $\mu$m. The fluorescence intensity of the resultant skin surface is measured non-invasively after stripping each skin layer using standard spectroscopy techniques. The process is repeated, with the induced fluorescence intensity due to the presence of DHA decreasing with each stripping.

The ideal concentration of DHA in the sunscreen composition produces a highly photo-protective layer that is bound just at the skin surface. Concentrations that are higher lead to excess amounts of the active compound binding within the stratum corneum, resulting in an increase in the time required for the DHA to be substantially shed, thus lengthening the time between sunscreen application and phototherapy. Although the stratum corneum of psoriatic skin is sloughed off at 8–10 times the rate of normal skin, it is also many times thicker. Therefore, active compounds which bind throughout the stratum corneum result in a higher level of staining, and may actually take longer to be completely sloughed off.

The desirable concentration of DHA in sunscreen compositions is defined as that necessary to provide substantial photo-protection to normal skin. For DHA, it is expected that a concentration of between about 5–20 percent by weight is appropriate, depending on the vehicles or agents used which may affect DHA staining of skin.

Because both the concentration of stratum corneum binding sites and kinetics of sloughing are expected to change during the clearing phase of phototherapy, the concentration of DHA may have to be selectively adjusted during treatment. Differential loss of DHA from affected skin regions is typically marked in early treatments, but as the regions clear, the rate of loss decreases and the DHA is retained longer. Depending on the patient, the frequency of application and concentration of DHA may therefore be changed during the course of phototherapy in accordance with the sloughing rates and binding site changes of the skin. It is a routine matter to make such frequency and concentration adjustments using the guidance given herein.

Additionally, a photosensitizing agent such as psoralen or a psoralen-based compound may be administered to a patient and used in combination with a topically-applied sunscreen. The compounds may be administered in one of the traditional modes (e.g., orally, parenterally, transdermally or transmucosally), in a sustained-release formulation using a biodegradable, biocompatible polymer, or by on-site delivery using micelles, gels and liposomes. Once administered, a sufficient time period is allowed to pass in order for the compound to be selectively retained in affected skin regions. Preferably, the compound is administered so that the ratio of drug retained in the affected and non-affected regions is maximized at approximately the same time that the ratio of the amount of sunscreen covering these regions is minimized. This allows for efficient treatment of the affected regions of skin using PDT.

Examples of photosensitizing agents which can be used in the method of the present invention include hematoporphyrin derivative (HPD), porfimer sodium (Photofrin), benzoporphyrin-derivative monoacid ring A (BPD-MA), mono-1-aspartyl chlorin e6 (NPe6), chloroaluminum sulfonated phthalocyanine and similar light-absorbing compounds which are selectively retained in affected skin regions and become activated (i.e., undergo photochemical reactions to produce cytotoxic singlet oxygen) following optical absorption. In addition, 5-aminolevulinic acid (ALA), a naturally-occurring precursor to the biosynthesized porphyrin Protoporphyrin IX, may be used as a photosensitizing agent. Examples of psoralen-based compounds which can be used in the method of the present invention include 8-MOP (methoxsalen, xanthotoxin), 5-methoxypsoralen (5-MOP, bergaptin), 7-methylpyridopsoralen, isopsoralen, and other isomeric and chemical derivative forms of psoralen.

4.2. Determination of Optical Fluence Levels for Phototherapy

The minimal erythema dose (MED) is the fluence, measured as energy per unit area, of radiation necessary to produce delayed erythema in a patient after irradiation. After receiving a photosensitizing agent, the amount of radiation needed to produce delayed erythema is called the minimal phototoxic dose (MPD). The phototoxic protection factor (PPF) refers to the ability of a sunscreen to protect the skin from photosensitized skin reactions, and is defined as the ratio of the MEDs or MPDs for skin protected with and without a sunscreen. Thus, the PPF provided by a sunscreen for a certain skin type can be determined by exposing the skin to UV fluence high enough to induce erythema in treated and untreated skin regions, and then determining the ratio of the optical fluences.

Because the sunscreen acts as a passive optical attenuating filter, the PPF is also simply related to the transmittance of light through the stratum corneum of protected skin. Following application of a sunscreen, accurate determination of the PPF for a particular skin sample allows the appropriate light level to be selected for phototherapy. Overestimation of the PPF may result in burning of the skin during treatment, while underestimation may reduce the effectiveness of phototherapy, thus prolonging treatment.

The PPF of a skin sample can be accurately determined using a non-invasive technique involving measuring the diffuse component of reflectance from a patient's skin (Wan et al., *J. Photochem. Photobiol.* 34:493–499, 1981; Kollias et al., *Biological Responses* to UVA Radiation, F. Urbach, ed., Valdenmar Pub. Co., Overland Park, Kans., 1992). When staining skin with DHA, the PPF is approximately equal to the square root of the ratio of diffuse light reflected from the skin before and after application of a sunscreen. The PPF can be expressed by the equation:

$$PPF = \sqrt{R_o/R_{sunscreen}} \quad (1)$$

Where $R_o$ and $R_{sunscreen}$ are the diffuse reflectance components of skin before and after application of a sunscreen, respectively, at the wavelength of interest. This result can also be expressed logarithmically as $$\log PPF = \tfrac{1}{2}(OD_{sunscreen} - OD_o) = (\Delta OD)/2 \quad (2)$$

where OD is the apparent optical density of the skin defined conventionally as $$OD = -\log R \quad (3)$$

where R is the diffuse reflectance at the wavelength of for photoprotection.

The PPF can therefore be measured by irradiating the surface of the skin with light having the appropriate wavelength, measuring the reflected light with a suitable photodetector, and then estimating the PPF using equation (1) above.

A sunscreen including an active compound provides a specific PPF for the skin, and may also stain the skin to a color depending on the skin type of the patient. These two factors can be compared for various skin types, and a "color chart" can be established which correlates the level of staining with the provided PPF. This allows approximation of the PPF by simple inspection of the level of skin staining, thus simplifying the procedure used to determine the appropriate level of optical radiation to be used during treatment.

4.3. Optical Irradiation of the Skin

Following the determination of the PPF and the appropriate level of optical irradiation, therapy may be conducted with standard treatment units well known in the art. For UVB phototherapy, sources emitting wavelengths less then 320 nm are used. For UVA and PUVA therapy, such units typically include fluorescent bulbs capable of emitting optical radiation peaked near 355 nm. The intensities of UVA doses are typically measured with photodetectors having maximum sensitivities between 350–360 nm. Within the area of treatment, the intensity of the radiation dose is kept relatively uniform. Infrared wavelengths emitted from the bulb are typically filtered out before reaching the area of treatment as they can heat the skin, causing discomfort to the patient during the therapy. Further details of the apparatus used for phototherapeutic treatments can be found in Honigsmann et al., *Dermatology in General Medicines,* 3rd ed, T. B. Fitzpatrick et al., eds., 1728–1754, 1987.

When photosensitizing agents are used in combination with topically-applied sunscreens, the wavelength of the incident optical radiation must lie within the absorption spectrum of the photosensitizing agent. Depending on the drug used, this region is typically between 320–700 nm. Preferably, a laser, such as a tunable dye or solid-state laser, a metal vapor laser, or a diode laser, is used as the light source. Lasers are often the most practical light source for treatment because their high power output at the appropriate drug-activating wavelength can minimize exposure times. In addition, laser light can easily be coupled into flexible optical fibers to simplify the delivery of light to the treatment region. Other light sources, such as fluorescent bulbs and solar simulators (Dougherty, et al., *Cancer Res.* 38:2628–2635, 1978) may also be used.

4.4. PPF Variation with the Concentration of the Active Compound

The PPF provided by a sunscreen will vary with the concentration of the active compound. The dependence of the PPF provided by DHA is a function of concentration can be determined by exposing a group of patients having skin types ranging from I–IV to PUVA therapy featuring optical fluence levels high enough to cause erythema. Solutions containing varying concentrations of DHA are used as photo-protectants for each patient, with a thin layer of solution at each concentration applied to a different area of skin in each patient. The MPDs of the different areas were measured by exposing nine 1 $cm^2$ sites in a single skin area to incrementally increased doses of UVA radiation, with the radiation being centered near 365 nm. Comparison of the MPDs from these areas with the MPD from an area free of DHA allows determination of the PPF, which can then be related to DHA concentration.

Such testing shows there is a linear relationship between DHA concentration and PPF such that an increase in the protection against erythema is provided by increasing concentrations of DHA.

The PPF provided by DHA can also be predicted using the non-invasive optical measurement described above. Experiments are conducted on two sunscreens by measuring the fluorescence excitation spectra of skin samples covered with a thin layer of sunscreen. Measurements are taken non-invasively by scanning the wavelength of an excitation light-source, followed by detection skin fluorescence at a single wavelength (Wan et al., *T. Photochem. Photobiol.* 34:493–499, 1981). The sunscreens to be used in such experiments should feature as an active compound DHA and dansyl chloride, a fluorescent molecule commonly used in standard assays of corneocyte sloughing kinetics (Takahashi et al., *J. Soc. Cosmetic Chem.* 38:321–331, 1987; Marks, *Cutaneous Investigation in Health and Disease,* Leveque ed., Mercel Dekker, Paris, 33–47, 1989). A Spex fluorometer featuring an excitation light source and a monochrometer must be fitted with an optical fiber bundle (Spex industries, Edison, N.J.) in order to deliver optical radiation to the sample of interest. Excitation wavelengths are chosen to match the peak of the absorption spectra of either DHA (350 nm) or dansyl chloride (335 nm). The excitation light passes through the monochrometer (4 nm bandpass) and into one arm of the fiber bundle, and used to irradiate the skin. Fluorescence from the skin is collected by the same fiber and passes through an emission monochrometer (4 nm bandpass) and into a detector. Excitation spectra are measured at the peak of the emission spectrum of either DHA (500 nm) or dansyl chloride (465 nm), and are corrected for a weak background of auto-fluorescence due to emission from unstained skin. The same instrument is used to measure skin reflectance spectra by setting the excitation and emission monochrometers to the same wavelength. By comparing the incident optical intensity with induced fluorescence or reflected intensity, the optical density of the active compound at the absorbing wavelength can be determined.

The change in OD, as defined in equation 3, is determined at 350 nm in various skin sites of living human volunteers stained with DHA, and is plotted as a function of the PPF. The PPF is determined by exposing the same skin sites to radiation at 350 nm after ingestion of 8-methoxypsoralen (8-MOP). The data is then compared to see if it fits in equation 2. An agreement between the data and the fit indicates the ability of the skin reflectance method of the present invention to accurately predict the PPF provided by an applied sunscreen using a simple, non-invasive measurement.

4.5. Rapid Desquamation of the Skin

Stratum-corneum sloughing can be investigated by monitoring the time-dependent decrease in fluorescence intensity from the skin after topical application of a sunscreen. A comparison of the time-dependent fluorescence intensities of psoriatic and non-affected skin samples stained with sunscreens including either DHA or dansyl chloride indicates that DHA-containing sunscreens allow phototherapeutic treatments to be carried out over a shorter period of time. The induced fluorescence intensity is decreased faster from psoriatic plaques stained with DHA, with the DHA being completely shed from the skin approximately 96 hours after application. In contrast, the dansyl chloride stain takes a longer period of time to be shed from the psoriatic skin. The rapid decrease in the time-dependent fluorescence intensity induced in psoriatic skin stained with DHA implies a more superficial binding of DHA to the stratum corneum in comparison with dansyl chloride.

During a phototherapeutic treatment, an approximately 72-hour time period separating the application of DHA and exposure of the skin to optical radiation will result in the optimization of the conditions for phototherapy. The natural sloughing off process of the psoriatic tissue leaves affected regions with minimal DHA protection, while non-affected skin is relatively well protected from optical radiation. This allows higher optical fluences to be used during the phototherapy, thus accelerating the treatment of the psoriatic condition. It should be noted that active means for desquamating stratum corneum can be used to increase the rate at which sunscreens containing DHA or other active compounds are shed from the skin. In particular, alpha-hydroxy acids, such as lactic acid, are effective desquamating agents. When applied before, during, or after application of a highly-substantive sunscreen, the period of time required for loss of the sunscreen will be reduced. Physical means to remove the skin may also be used.

4.6. Use of DRA in Phototherapy

The absorption spectrum of DHA-stained skin extends from roughly 300–600 nm, and is peaked near 350 nm. The DHA staining is a yellow-brown or orange color, and is generally cosmetically acceptable because it mimics natural tanned skin. During PUVA therapy, the skin is typically most sensitive to optical wavelengths near 320 to 330 nm. The overlap of these two spectra indicates that the active and most harmful optical wavelengths used in PUVA therapy will be preferentially absorbed by DHA. Conventional DHA preparations have poor absorbance in the UVB range (Levy, J. Am. Acad. Dermatol. 27:989–993, 1992). DHA absorbance is pH dependent, and a colored yellow product has been observed to appear at high, but still safe, pH levels in the human skin. This implies a shift in the absorption spectrum toward 300 nm for DHA incorporated in high pH environments. A high pH DHA preparation may therefore be used in a sunscreen as a UVB photo-protectant. An effective sunscreen for UVB phototherapy can also be made by using an increased concentration of DHA, resulting in a higher optical absorbance at wavelengths near 320 nm. Alternatively, active compounds such as Glycerylaminobenzoate, Amyl-p-dimethylamino benzoate (Padimate-A), 2-Ethyl-hexyl-p-dimethylamino benzoate (Padimate-O), and 3,3,5-Trimethyl-cyclohexyl-salicylate (homosalate), absorb light having wavelengths closer to the UVB range. These active compounds, when included in highly-substantive sunscreens, are useful photo-protectants.

Following administration of a photosensitizing agent, there is often appreciable uptake of the drug in the non-affected regions of skin, making it necessary to attenuate optical radiation incident on these regions during therapy. It is therefore desirable to use a sunscreen containing an active component having substantial optical absorption at the drug-activating wavelength of the light source. DHA-stained skin exhibits partial optical absorption between 320–600 nm, and thus can be used in combination with a variety of photo-sensitizing agents for treatment of affected regions of skin.

The following examples of the compositions of the present invention are presented for purposes of illustration and description. They are not intended to be exhaustive or to limit the invention to the precise form disclosed.

5. EXAMPLES

5.1 Example 1

Compositions Containing DRA

Several DHA-containing compositions were made according to the formulations delineated in Table 1. (name provided in accordance with (CTFA)). All of the percentages in Table 1 represent a percentage by weight. Composition No. 4 is a preferred embodiment of the present invention.

TABLE 1

SUNSCREEN LOTIONS CONTAINING DHA

| Ingredient | Composition 1 | Composition 2 | Composition 3 | Composition 4 | Composition 5 | Composition 6 |
|---|---|---|---|---|---|---|
| Cetyl Alcohol | 2.00 | 2.00 | 2.00 | 1.50 | 1.50 | 1.50 |
| Liponate NPGC-2 | 5.00 | 5.00 | 5.00 | 5.00 | 5.00 | 5.00 |
| Hetester PHA | 5.00 | 5.00 | 5.00 | — | 5.00 | 5.00 |
| BHT | 0.10 | 0.10 | 0.10 | 0.10 | 0.10 | 0.10 |
| Ganex WP-660 | 1.50 | 1.50 | 1.50 | — | 1.50 | 1.50 |
| DC556 | 1.50 | 1.50 | 1.50 | 3.00 | 1.50 | 1.50 |
| Propyl Paraben | 0.10 | 0.10 | 0.10 | — | 0.10 | 0.10 |
| Amphisol | 1.50 | 1.50 | 1.50 | 1.50 | 1.50 | 1.50 |
| Brij 721 | 1.00 | 1.00 | 1.00 | 1.00 | 1.00 | 1.00 |
| Polyolprepolymer | — | — | — | 10.00 | — | — |
| Cellosize PCG-10 | 0.50 | 0.50 | 0.50 | 0.30 | 0.50 | 0.50 |
| Deionized Water | 55.80 | 54.80 | 49.80 | 40.90 | 60.40 | 55.40 |
| Sorbic Acid | 0.10 | 0.10 | 0.10 | — | 0.10 | 0.10 |
| Na$_2$EDTA | 0.10 | 0.10 | 0.10 | — | — | — |
| Tween 20, NE | 1.50 | 1.50 | 1.50 | 1.50 | 1.50 | 1.50 |
| Methyl Paraben | 0.20 | 0.20 | 0.20 | 0.20 | 0.20 | 0.20 |
| 1,3-Butylene Glycol | 5.00 | 5.00 | 5.00 | 5.00 | 5.00 | 5.00 |

TABLE 1-continued

SUNSCREEN LOTIONS CONTAINING DHA

| Ingredient | Composition 1 | Composition 2 | Composition 3 | Composition 4 | Composition 5 | Composition 6 |
|---|---|---|---|---|---|---|
| Deionized Water | 5.00 | 10.00 | 15.00 | 15.00 | 5.00 | 11.00 |
| Na-Metabisulfite | 0.10 | 0.10 | 0.10 | — | 0.10 | 0.10 |
| Dihydroxyacetone | 5.00 | 10.00 | 15.00 | 15.00 | 5.00 | 10.00 |
| Lactic Acid | — | — | — | 2.50 | — | — |

The compositions 1–6 above are sunscreen lotions with varying percentages of DHA. These compositions were prepared as follows:

1. Combine the first ten ingredients listed in Table 1, except for the Amphisol, and heat the mixture to 80°–85° C. Add the Amphisol to the heated mixture and stir until the mixture is homogeneous.
2. Disperse the Cellosize PCG-10 in deionized water at room temperature. Slowly heat to about 80° C. Mix until "jelled" and then add the appropriate amounts of sorbic acid, $Na_2EDTA$, Tween 20Nf, and methyl paraben.
3. Transfer the mixtures of Steps 1 and 2 into a homomixer and mix for 4–5 minutes at ½ speed.
4. Allow mixture of Step 3 to cool to about 45° C.
5. Combine the last five ingredients listed in Table 1. Heat this mixture to 40° C. in order to dissolve. Add this mixture to the mixture of Step 4 (45° C.).
6. Cool mixture of Step 5 to room temperature.

What is claimed is:

1. A topical composition suitable for use in phototherapeutic treatment of proliferative skin disorders which comprises:

(a) dihydroxyacetone;
   (b) 0.2 to 20 per cent of a penetration attenuator; and
   (c) a cosmetically or pharmaceutically acceptable carrier.

2. The composition of claim 1, wherein dihydroxyacetone is present in an amount of about 10 to about 20 percent by weight.

3. The composition of claim 1, wherein DHA is present in an amount of about 15 percent by weight.

4. The composition of claim 1, wherein the penetration attenuator comprises a polymeric material.

5. The composition of claim 1, wherein the penetration attenuator comprises a polyolprepolymer.

6. The composition of claim 1, wherein the penetration attenuator is present in an amount of about 5.0 to about 15.0 percent by weight.

7. The composition of claim 1, which further comprises an acidic component.

8. The composition of claim 7, wherein the acidic component comprises an inorganic or organic acid.

9. The composition of claim 7, wherein the acidic component comprises an alpha-hydroxy acid or derivatives thereof.

10. The composition of claim 9, wherein the acidic component comprises lactic acid.

11. The composition of claim 7, wherein the acidic component is present in an amount of about 0.1 to about 20.0 percent by weight.

12. The composition of claim 7, wherein the acidic component is present in an amount of about 1.0 to about 5.0 percent by weight.

13. The composition of claim 7, wherein the acidic component is present in an amount of about 2.5 percent by weight.

14. The composition of claim 1, wherein the proliferative skin disorder is psoriasis, mycosis fungoides, eczema, actinic keratosis, or lichen planus.

15. The composition of claim 1 which further comprises a photosensitizing agent.

* * * * *